United States Patent [19]

Helwig et al.

[11] Patent Number: 4,785,107
[45] Date of Patent: Nov. 15, 1988

[54] 3-TERT-BUTYL-4-HYDROXYPHENYLPROPIONIC ACID AMINO-ALKYLAMIDE DERIVATIVES

[75] Inventors: Reinhard Helwig, Ludwigshafen; Peter Neumann, Wiesloch; Herbert Bender, Boehl-Iggelheim; Alexander Aumueller, Ludwigshafen; Hubert Trauth, Dudenhofen, all of Fed. Rep. of Germany

[73] Assignee: BASF Aktiengesellschaft, Rheinland-Pfalz, Fed. Rep. of Germany

[21] Appl. No.: 873,706

[22] Filed: Jun. 12, 1986

[30] Foreign Application Priority Data

Jun. 15, 1985 [DE] Fed. Rep. of Germany ....... 3521558

[51] Int. Cl.$^4$ ................. C07C 121/78; C07C 103/44; C07D 213/73
[52] U.S. Cl. .................................... 546/244; 558/414; 564/170
[58] Field of Search ........................ 558/414; 546/244; 564/170

[56] References Cited

U.S. PATENT DOCUMENTS 4,066,610  1/1978  Kiss et al. .................... 260/42.21

FOREIGN PATENT DOCUMENTS 3521558 12/1986  Fed. Rep. of Germany .
 919711  2/1963  United Kingdom .

*Primary Examiner*—Anton H. Sutto
*Attorney, Agent, or Firm*—Oblon, Fisher, Spivak, McClelland & Maier

[57] ABSTRACT

The novel phenol derivatives of the general formula (I)

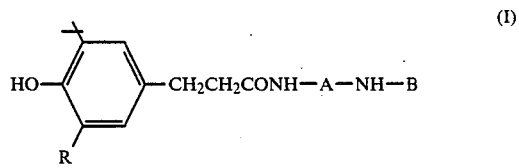

where R is hydrogen, straight-chain or branched $C_1$–$C_8$-alkyl or cycloalkyl, A is a bridge member and B is a radical of the formula

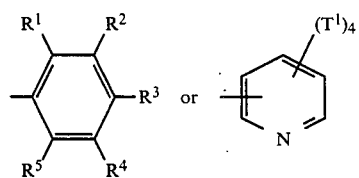

where $R^1$, $R^2$, $R^3$, $R^4$, $R^5$ and $T^1$ independently of one another are each hydrogen, $C_1$–$C_8$-alkyl, halogen, CN, $COOT^2$ or $CONHT^2$, with the proviso that one or more of the radicals $R^1$, $R^2$, $R^3$, $R^4$, $R^5$ and $T^1$ are halogen, CN, $COOT^2$ and $CONHT^2$ and $T^2$ is $C_1$–$C_8$-alkyl, are useful for stabilizing organic material, in particular polyolefins, to degradation by oxidation.

13 Claims, No Drawings

3-TERT-BUTYL-4-HYDROXYPHENYLPROPIONIC ACID AMINO-ALKYLAMIDE DERIVATIVES

Phenolic compounds which carry alkyl substituents in the position adjacent to the hydroxyl group have long been known as antioxidants. When added to organic substances, in particular to organic polymers, they considerably increase the stability of these substances to oxygen. Good antioxidants must meet a number of requirements, such as high activity, high heat stability, little tendency to become discolored even at elevated temperatures, low volatility and good compatibility with the material being stabilized.

It is an object of the present invention to provide phenol derivatives which meet the requirements and criteria set by the application.

We have found that this object is achieved by phenol derivatives of the formula (I)

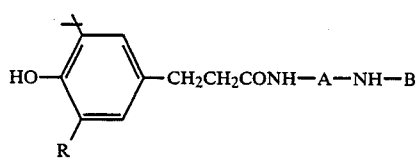

where R is hydrogen, straight-chain or branched $C_1$–$C_8$-alkyl or cycloalkyl, A is a bridge member and B is a radical of the formula

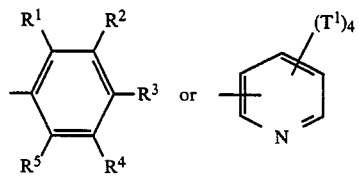

where $R^1$, $R^2$, $R^3$, $R^4$ and $R^5$ and $T^1$ independently of one another are each hydrogen, $C^1$–$C^8$-alkyl, halogen, —CN, —COOT² or —CONHT², with the proviso that one or more of the radicals $R^1$, $R^2$, $R^3$, $R^4$, $R^5$ and $T^1$ are halogen, CN, COOT² or CONHT², and - T² is $C^1$–$C^8$-alkyl.

Specific examples of radicals R are $CH^3$, $C^2H^5$, n-$C_3H_7$, i-$C_3H_7$, i-$C_4H_9$, t-$C_4H_9$, tert-amyl, i-$C_6H_{13}$, i-$C_8H_{17}$,

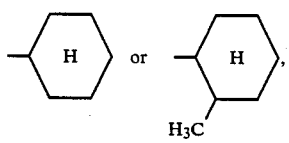

methyl, iso- and tert-radicals, in particular methyl and t-$C_4H_9$, being preferred.

Suitable bridge members A are straight-chain or branched $C_2$–$C_{16}$-alkylene, cycloalkylene and cycloalkylene containing alkylene. Examples of bridge members A are —(CH₂)₂—, —(CH₂)₃—, —(CH₂)₆—,

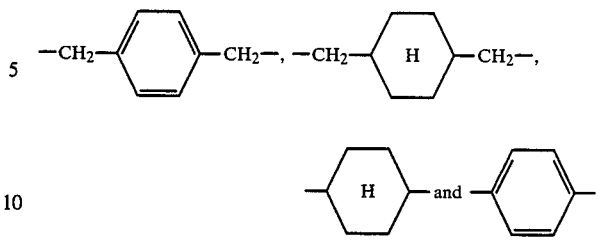

of which —CH₂CH₂— and —CH₂CH₂CH₂— are preferred.

In addition to being hydrogen, T² is, for example, $CH_3$, $C_2H_5$, $C_3H_7$, $C_4H_9$, $C_6H_{13}$, $C_8H_{17}$.

$R^1$ to $R^5$ and $T^1$ are each preferably hydrogen, $C_1$–$C_4$-alkyl, chlorine or CN.

The novel compounds can be synthesized by known processes. In the most advantageous process, a compound of the formula

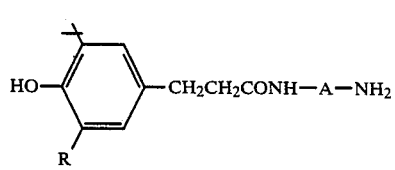

is reacted with a halogen-containing compound of the formula

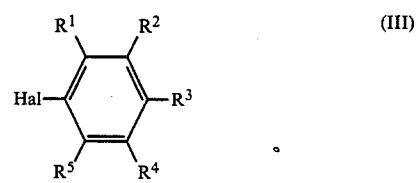

or

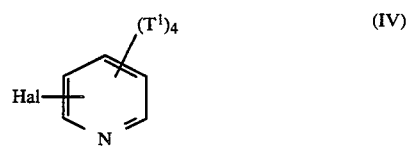

in the presence of an acid acceptor, with elimination of hydrogen halide. Halogen atoms which are preferably eliminated are fluorine and cholorine.

However, it is also possible to react an ester of the formula

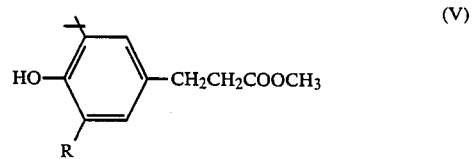

or the corresponding ethyl ester with an amino compound of the formula

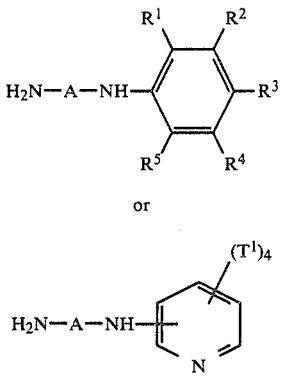

or $$H_2N-A-NH-\overset{(T^1)_4}{\underset{N}{\bigcirc}}\quad (VII)$$

with elimination of methanol or ethanol.

The halogenated aromatics or pyridine derivatives required for the corresponding reactions are described in the literature. The 3,5-dialkyl-4-hydroxyphenylpropionic acid aminoalkylamides (II) are described in the literature (eg. German Laid-Open Application DOS No. 3,500,058) or can be prepared in a similar manner.

The Examples which follow illustrate the preparation. Parts and percentages are by weight, unless stated otherwise.

The compounds according to the invention are useful for stabilizing organic material, in particular plastics. When used in plastics, they are suitable both as processing stabilizers and as long-term stabilizers. The agents (I) are added to the plastics to be stabilized in a concentration of from 0.01 to 5, preferably from 0.02 to 2, % by weight, before, during or after polymer formation.

Mixing of the novel compounds with the plastics to be stabilized can be carried out using any conventional apparatus and method for mixing stabilizers or other additives into polymers.

The plastics stabilized by the novel compounds can, if necessary, contain further additives, for example co-stabilizers, light stabilizers, metal deactivators, antistatic agents, flame-retardant agents, lubricants, plasticizers, crosslinking agent, dyes, pigments and fillers.

Examples of co-stabilizers are sulfur-containing antioxidants, such as dilauryl thiodipropionate, dimyristyl thiodipropionate, distearyl thiodipropionate, pentaerythritol tetrakis-(β-laurylthiopropionate), pentaerythritol tetrakis(β-hexylthiopropionate) etc.; and phosphorus-containing compounds, such as tris(nonylphenyl) phosphite, distearylpentaerythritol diphosphite, tris(2,4-di-tert-butylphenyl) phosphite, tris(2-tert-butyl-4-methylphenyl) phosphite, bis(2,4-di-tert-butylphenyl)pentaerythritol diphosphite, tetrakis (2,4-di-tert-butylphenyl)-4,4'-biphenylene diphosphite, etc.

Examples of light stabilizers which may be used together with the novel compounds are 2-(2'-hydroxyphenyl)-benzotriazoles, 2-hydroxybenzophenones, aryl esters of hydroxybenzoic acids, α-cyanocinnamic acid derivatives, nickel compounds and oxalic acid dianilides, as well as compounds which contain a 2,2,6,6-tetraalkylpiperidinyl group, eg. bis-2,2,6,6-tetramethyl-4-piperidinyl sebacate, bis-1,2,2,6,6-pentamethyl-4-piperidinyl sebacate, poly(N, β-hydroxyethyl-2,2,6,6-tetramethyl-4-hydroxypiperidinesuccinate) or poly-[6-[(1,1,3,3-tetramethylbutyl)imino]-1,3,5-triazine-2,4-diyl][2-(2,2,6,6-tetramethylpiperidinyl)-imino]-hexamethylene-[4-(2,2,6,6-tetramethylpiperidinyl)-imino].

Examples of suitable organic polymers which can be stabilized by the novel compounds are polymers of mono- and diolefins, such as low density or high density polyethylene, linear low density polyethylene, and polypropylene, polyisobutylene, polybut-1-ene, polymethylpent-1-ene, polyisoprene or polybutadiene, and copolymers of mono- and diolefins or blends of the stated polymers; copolymers of mono- or diolefins with other vinyl monomers, eg. ethylene/alkyl acrylate copolymers, ethylene/alkyl methacrylate copolymers, ethylene/vinyl acetate copolymers or ethylene/acrylic acid copolymers; polystyrene; copolymers of styrene or α-methylstyrene with dienes or acryl derivatives, such as styrene/butadiene, styrene/acrylonitrile, styrene/ethyl methacrylate, styrene/butadiene/ethyl acrylate and styrene/acrylonitrile/methyl acrylate copolymers; halogen-containing polymers, such as polyvinyl chloride, polyvinyl fluoride or polyvinylidene fluoride, and copolymers with the corresponding monomers; polymers derived from α, β-unsaturated acids and their derivatives, such as polyacrylates and polymethacrylates, polyacrylamides and polyacrylonitriles; polymers derived from unsaturated alcohols and amines and their acyl derivatives or acetals, such as polyvinyl alcohol or polyvinyl acetate; and polyurethanes, nylons, polyureas, polyesters, polycarbonates and polyether sulfones.

A. EXAMPLES OF STARTING COMPOUNDS 1. 3-tert-Butyl-4-hydroxy-5-methylphenylpropionic acid 2-aminoethylamide 125 g of methyl 3-tert-butyl-4-hydroxy-5-methylphenylpropionate and 300 g of ethylenediamine are heated together at 110° C. for 5 hours, after which a vacuum is applied and the resulting methanol and the excess ethylenediamine are distilled off. 0.3 l of toluene are added to the residue, and the mixture is left to stand at room temperature for one hour. The precipitate is filtered off under suction and dried to give 118 g of the product which, after recrystallization from ethyl acetate, has a melting point of 156°–159° C.

2. 3,5-di-tert-Butyl-4-hydroxyphenylpropionic acid 3-aminopropylamide 146 g of methyl 3,5-di-tert-butyl-4-hydroxyphenylpropionate and 370 g of 1,3-propanediamine are heated together at 130° C. for 11 hours, after which the mixture is evaporated down under reduced pressure. The residue melts at 75°–80° C.

3. 4-(2-Aminoethylamino)-2,3,5,6-tetrachlorobenzonitrile 55 g of pentachlorobenzonitrile are introduced into 300 g of ethylenediamine at room temperature in such a way that the temperature does not exceed 30° C. The mixture is then stirred for a further half an hour at room temperature, after which 0.75 l of ice water is slowly added and stirring is continued for 15 minutes. The precipitate is filtered off under suction, washed with water and dried to give 55 g of product which, when recrystallized from toluene with the addition of active carbon, has a melting point of 140°–144° C.

B. PREPARATION EXAMPLES

EXAMPLE 1

4-[2-(3,5-di-tert-Butyl-4-hydroxyphenylpropionamido)ethylamino]-2,3,5,6-tetrachlorobenzonitrile 27.6 g of pentachlorobenzonitrile and 32 g of 3,5-di-tert-butyl-4-hydroxyphenylpropionic acid 2-aminoethylamide are reacted with 11 g of triethylamine in 200 g of N-methylpyrrolidone for 7 hours at 100° C., after which 500 g of water and 400 g of toluene are added, and the toluene phase is separated off while still hot and evaporated down under reduced pressure. The residue is boiled with 0.15 l of ethanol, and the mixture is left to stand overnight at room temperature. The precipitate is then filtered off under suction and dried. After recrystallization from toluene, the product melts at 173°–175° C.

EXAMPLE 2

4-[2-(3,5-di-tert-butyl-4-hydroxyphenylpropionamido)ethylamino]-2,5,6-trichloroisophthalodinitrile 26.6 g of tetrachloroisophthalodinitrile and 32 g of 3,5-di-tert-butyl-4-hydroxyphenylpropionic acid 2-aminoethylamide are reacted with 11 g of triethylamine in 200 g of N-methylpyrrolidone for 2 hours at 80° C. After the mixture has cooled, 1 l of water is added, the mixture is extracted with 0.5 l of toluene and the toluene phase is dried and evaporated down. The residue is boiled with 0.25 l of ethanol and stirred for a further three hours at room temperature. The precipitate is filtered off under suction and dried to give 17 g of a product of melting point 209°–211° C.

EXAMPLE 3

3-[2-(3,5-di-tert-butyl-4-hydroxyphenylpropionamido)ethylamino]-4,5,6-trichlorophthalodinitrile 26.6 g of tetrachlorophthalodinitrile and 32 g of 3,5-di-tert-butyl-4-hydroxyphenylpropionic acid 2-aminoethylamide are heated with 11 g of triethylamine in 200 g of N-methylpyrrolidone for 4 hours at 80° C., after which 1 l of water and 0.2 l of toluene are added, and the toluene phase is separated off at 90° C. The product crystallizes out on cooling. Recrystallization from toluene in the presence of active carbon gives a product of melting point 166°–168° C.

EXAMPLE 4

[2-(3,5-di-tert-Butyl-4-hydroxyphenylpropionamido)-ethylamino]-trichloronicotinonitrile

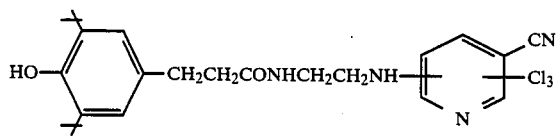

24.2 g of tetrachloronicotinonitrile and 32 g of 3,5-di-tert-butyl-4-hydroxyphenylpropionic acid 2-aminoethylamide are reacted with 11 g of triethylamine in the manner described in Example 3, and the mixture is worked up. The product has a melting point of 188°–193° C.

EXAMPLE 5

[2-(3,5-Di-tert-butyl-4-hydroxyphenylpropionamido)-ethylamino]-trichloronicotinonitrile.

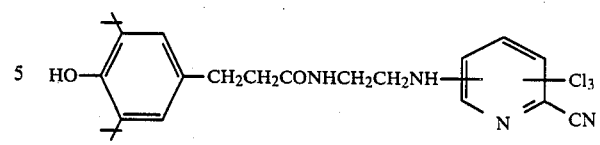

24.2 g of tetrachloropicolinonitrile and 32 g of 3,5-di-tert-butyl-4-hydroxyphenylpropionic acid 2-aminoethylamide are reacted with 11 g of triethylamine in 0.2 l of N-methylpyrrolidone at 80° C. for 4 hours. 0.5 l of water and 0.4 l of toluene are added, after which the mixture is stirred for a short time at 90° C. and the hot toluene phase is separated off and evaporated down. The residue is boiled in a 1:1 mixture of toluene and petroleum ether, and the mixture is left to stand for a few hours at room temperature. The precipitate is filtered off under suction and dried, and the product has a melting point of 185°–189° C.

EXAMPLE 6

[2-(3,5-di-tert-Butyl-4-hydroxyphenylpropionamido)-ethylamino]-trichloroisonicotinonitrile

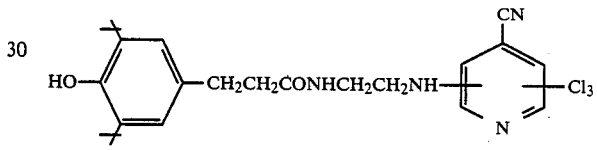

24.2 g of tetrachloroisonicotinonitrile and 32 g of 3,5-di-tert-butyl-4-hydroxyphenylpropionic acid 2-aminoethylamide are reacted with 11 g of triethylamine in 0.2 l of N-methylpyrrolidone in the manner described in Example 2. The toluene extract is evaporated down, and the residue is recrystallized from a 4:1 mixture of cyclohexane and toluene with the addition of active carbon. The product has a melting point of 150°–160° C.

EXAMPLE 7

3,5-di-tert-Butyl-4-hydroxyphenylpropionic acid 2-(tetrachloropyridineamino)-ethylamide

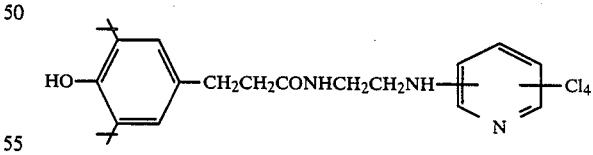

25.2 g of pentachloropyridine and 32 g of 3,5-di-tert-butyl-4-hydroxyphenylpropionic acid 2-aminoethylamide are reacted with 11 g of triethylamine in 0.2 l of N-methylpyrrolidone at 50° C. for 4 hours. 1 l of water is added, after which the mixture is extracted with 0.3 l of toluene, the extract is filtered over active carbon, and the filtrate is evaporated down under reduced pressure. The residue is dissolved in an ethanol/water mixture, and the solution is left to stand until crystallization takes place. The dry precipitate has a melting point of 117°–122° C.

EXAMPLE 8

6-[2-(3,5-di-tert-Butyl-4-hydroxyphenylpropionamido)ethylamino]-2-chloro-4-methylnicotinonitrile

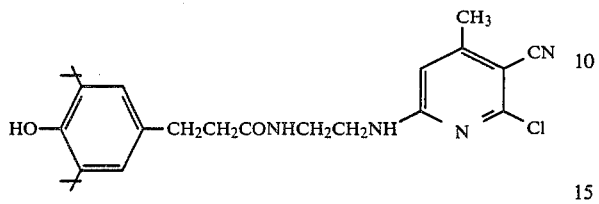

18.7 g of 2,6-dichloro-4-methylnicotinonitrile and 32 g of 3,5-di-tert-butyl-4-hydroxyphenylpropionic acid 2-aminoethylamide are reacted with 10.1 g of triethylamine in 0.2 l of N-methylpyrrolidone at 50° C. for 8 hours, after which 1 l of water and 0.4 l of toluene are added, the toluene phase is separated off, dried and filtered over active carbon, and the filtrate is evaporated down. The residue is dissolved in 100 ml of hot ethanol, and 1 l of petroleum ether is slowly added to the solution. The mixture is cooled, and the precipitate is filtered off under suction and dried to give a product of melting point 162°–165° C.

EXAMPLE 9

4-[2-(3,5-di-tert-Butyl-4-hydroxyphenylpropionamido)ethylamino]-benzonitrile 13.75 g of 4-chlorobenzonitrile and 32 g of 3,5-di-tert-butyl-4-hydroxyphenylpropionic acid 2-aminoethylamide are reacted with 12.9 g of quinoline in 0.2 l of N-methylpyrrolidone at 180° C. for 8 hours, after which the mixture is cooled, stirred into 0.5 l of 7% strength hydrochloric acid and extracted with 0.2 l of toluene, the toluene extract is evaporated down and the residue is purified over a silica gel column (mobile phase: ethyl acetate). The product has a melting point of 146°–148° C.

EXAMPLE 10

2-Chloro-6-[2-(3,5-di-tert-butyl-4-hydroxyphenylpropionamido)-ethylamino]-benzonitrile 17.2 g of 2,6-dichlorobenzonitrile and 32 g of 3,5-di-tert-butyl-4-hydroxyphenylpropionic acid 2-aminoethylamide in 150 ml of quinoline are reacted at 200° C. for 4 hours. The solution is cooled and then stirred into 1 l of 10% strength hydrochloric acid, the mixture is extracted with 0.4 l of toluene and the dried toluene phase is evaporated down. Residual volatile components are removed by heating for 2 hours at 180° C. under reduced pressure from an oil pump. The residue is purified by column chromatography (silica gel/methylene chloride). The product has a melting point of 164°–167° C.

The following compounds (I) are prepared similarly to Examples 1 to 10:

TABLE 1

| | Compounds of the formula I | | |
|---|---|---|---|
| Example No. | R | A | B |
| 11 | CH$_3$ | —(CH$_2$)$_2$— | tetrachloro-cyanophenyl |
| 12 | CH$_3$ | —(CH$_2$)$_3$— | tetrachloro-dicyanophenyl (CN, Cl, CN, Cl, Cl) |
| 13 | CH$_3$ | —(CH$_2$)$_2$— | pyridyl-Cl$_3$-CN |
| 14 | t-C$_4$H$_9$ | —(CH$_2$)$_3$— | tetrachloro-cyanophenyl |
| 15 | t-C$_4$H$_9$ | —(CH$_2$)$_2$— | —C$_6$H$_4$—COOC$_4$H$_9$ |

C. Examples of use

C1. Testing the long-term stability of polypropylene

Polypropylene containing 0.1% of calcium stearate (eg. Novolen 1100), and, as an antioxidant, 0.1% of the compounds stated in Table 2, are converted to a homogeneous mixture in a high-speed mixer and, by means of the Type ET 20 laboratory extruder from Weber, the mixture is extruded at a melt temperature of 220° C. and granulated. The granules are molded at 220° C. to give specimens measuring 20×20×1 mm, which are stored at 149° C. in a through-circulation dryer with a fresh air feed.

In accordance with DIN 53,383, the time taken for local embrittlement to occur is determined as the oxidation stability time. A few examples are summarized in Table 2.

TABLE 2

| Compound from Example | Oxidation stability time [h] | Color when embrittlement begins |
|---|---|---|
| 1 | 680 | pale yellowish |
| 2 | 530 | pale yellow |
| 5 | 520 | pale yellow |
| 6 | 460 | brownish |
| 8 | 400 | yellowish |

C2. Testing the processing stability of polypropylene

Polypropylene containing 0.1% of calcium stearate (eg. Novolen 1100), and 0.1% of the compound stated in Table 3, are converted to a homogeneous mixture in a highspeed mixer and, by means of Type ET 20 laboratory extruder from Weber, the mixture is extruded at a melt temperature of 250° C. and granulated. The granules are subjected to a further seven passes through the extruder. After each pass through the extruder, a sample of the granules is taken and its melt flow index MFI 230° C./2160 g (g/10 min) according to DIN 53,735 is measured.

TABLE 3

| Compound from | Melt flow index [g/10 min] after extruder pass No. | | | |
|---|---|---|---|---|
| Example | 1 | 3 | 5 | 8 |
| 1 | 4.63 | 7.2 | 10.1 | 14.45 |
| 2 | 4.6 | | | 15.6 |
| no antioxidant | 5.4 | 9.5 | 17.0 | 26.0 |

C3. Testing the gas fading

Polypropylene containing 0.1% of calcium stearate (eg. Novolen 1100), and 0.1% of the compound described in Example 1, are converted to a homogeneous mixture in a high-speed mixer and, by means of a type ET 20 laboratory extruder from Weber, the mixture is extruded at a melt temperature of 250° C. and granulated. The granules are spun to fibers (about 30 dtex) on a spinning apparatus, and a sample of about 10 g of these fibers in each case is exposed for 10 minutes, in a combustion box (DIN 52,906), to the exhaust gases from a propane gas flame. The flame is adjusted so that the temperature in the direct environment of the fibers is about 110° C. After exposure to the gas, the resulting change in shade is assessed.

| Stabilizer | Fiber color after exposure to gas |
|---|---|
| Compound from Example 1 | colorless |
| Irganox 1010 | pink |
| No stabilizer | pale gray |

We claim:

1. A phenol derivative of the formula (I)

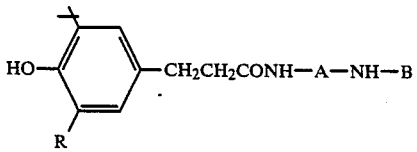                                                      (I)

where R is $CH_3$, $C_2H_5$, n-$C_3H_7$, i-$C_4H_9$, t-$C_4H_9$, tert-amyl, i-$C_6H_{13}$, i-$C_8H_{17}$,

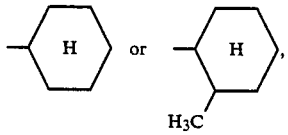

A is —$(CH_2)_2$—, —$(CH_2)_3$—, —$(CH_2)_6$—,

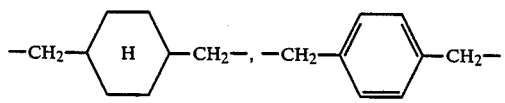

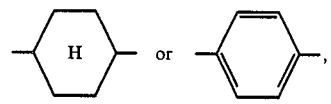

and B is a radical of the formula

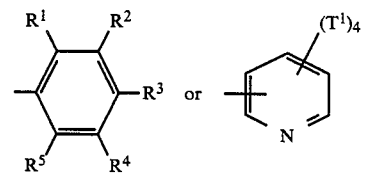

where $R^1$, $R^2$, $R^3$, $R^4$, $R^5$ and $T^1$ independently of one another are each hydrogen, $C_1$-$C_8$-alkyl, halogen, CN, $COOT^2$ or $CONHT^2$, with the proviso that one or more of the radicals $R^1$, $R^2$, $R^3$, $R^4$, $R^5$ and $T^1$ are halogen, CN, $COOT^2$ or $CONHT^2$, and $T^2$ is $C_1$-$C_8$-alkyl.

2. A compound as claimed in claim 1, wherein R is methyl or tert-butyl.

3. A compound as claimed in claim 1, wherein A is —$CH_2CH_2$— or —$CH_2CH_2CH_2$—.

4. A compound as claimed in claim 2, wherein A is —$CH_2CH_2$— or —$CH_2CH_2CH_2$—.

5. A compound as claimed in claim 1, wherein $R^1$, $R^2$, $R^3$, $R^4$, $R^5$ and $T^1$ independently of one another are each hydrogen, $C_1$-$C_4$-alkyl, chlorine or CN.

6. A compound as claimed in claim 2, wherein $R^1$, $R^2$, $R^3$, $R^4$, $R^5$ and $T^1$ independently of one another are each hydrogen, $C_1$-$C_4$-alkyl, chlorine or CN.

7. A compound as claimed in claim 3, wherein $R^1$, $R^2$, $R^3$, $R^4$, $R^5$ and $T^1$ independently of one another are each hydrogen, $C_1$-$C_4$-alkyl, chlorine or CN.

8. A compound as claimed in claim 4, wherein $R^1$, $R^2$, $R^3$, $R^4$, $R^5$ and $T^1$ independently of one another are each hydrogen, $C_1$-$C_4$-alkyl, chlorine or CN.

9. A phenol derivative of the formula

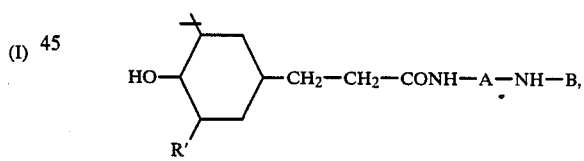

in which R' is methyl or tert-butyl, A is —$CH_2CH_2$— or —$CH_2CH_2CH_2$— and B is a radical of the formula

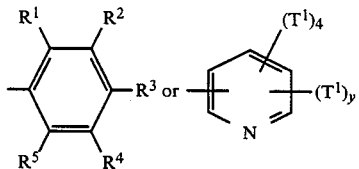

where $R^1$, $R^2$, $R^3$, $R^4$, $R^5$ and $T^1$ independently of one another are each hydrogen, $C_1$-$C_4$-alkyl, chlorine or CN, and one or more of the radicals $R^1$, $R^2$, $R^3$, $R^4$, $R^5$ and $T^1$ are chlorine or CN.

10. A phenol derivative as claimed in claim 9, wherein $R^1$, $R^2$, $R^3$, $R^4$, $R^5$ and $T^1$ independently of one another are each hydrogen, methyl, chlorine or CN, and one or more of the radicals $R^1$, $R^2$, $R^3$, $R^4$, $R^5$ and $T^1$ are chlorine or CN.
11. A phenol derivative as claimed in claim 9, of the formula
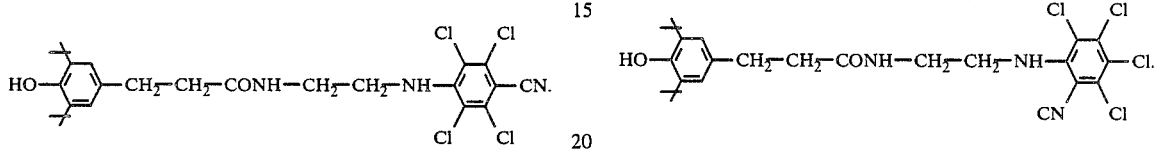
12. A phenol derivative as claimed in claim 9, of the formula
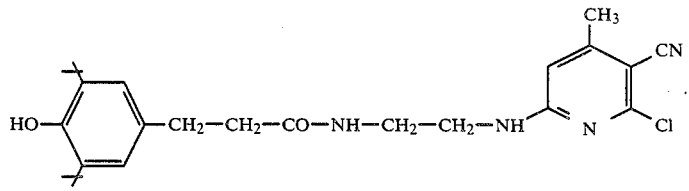
13. A phenol derivative of the formula